(12) United States Patent
Razavi et al.

(10) Patent No.: US 9,380,940 B2
(45) Date of Patent: Jul. 5, 2016

(54) METHOD AND SYSTEM FOR DISPLAYING A THREE DIMENSIONAL VISUALIZATION OF CARDIAC MOTION

(71) Applicant: Pacesetter Inc., Sunnyvale, CA (US)

(72) Inventors: Hoda Razavi, San Jose, CA (US); Yelena Nabutovsky, Mt. View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 173 days.

(21) Appl. No.: 14/270,176

(22) Filed: May 5, 2014

(65) Prior Publication Data

US 2015/0313510 A1     Nov. 5, 2015

(51) Int. Cl.
| | |
|---|---|
| *G06K 9/00* | (2006.01) |
| *A61B 5/00* | (2006.01) |
| *A61B 5/11* | (2006.01) |
| *A61B 5/0402* | (2006.01) |
| *A61B 5/029* | (2006.01) |
| *A61B 5/042* | (2006.01) |
| *A61B 5/06* | (2006.01) |

(52) U.S. Cl.
CPC .............. *A61B 5/00* (2013.01); *A61B 5/0044* (2013.01); *A61B 5/029* (2013.01); *A61B 5/0402* (2013.01); *A61B 5/0422* (2013.01); *A61B 5/061* (2013.01); *A61B 5/11* (2013.01); *A61B 5/1102* (2013.01); *A61B 5/4519* (2013.01); *A61B 5/7289* (2013.01)

(58) Field of Classification Search
None
See application file for complete search history.

(56) References Cited

U.S. PATENT DOCUMENTS

| | | |
|---|---|---|
| 5,391,199 A | 2/1995 | Ben-Haim |
| 6,233,476 B1 | 5/2001 | Strommer et al. |
| 6,301,496 B1 | 10/2001 | Reisfeld |
| 6,609,027 B2 | 8/2003 | Kroll et al. |
| 6,633,686 B1 | 10/2003 | Bakircioglu et al. |
| 6,728,562 B1 | 4/2004 | Budd et al. |
| 6,751,492 B2 | 6/2004 | Ben-Haim |
| 6,978,168 B2 | 12/2005 | Beatty et al. |
| 7,197,354 B2 | 3/2007 | Sobe |
| 7,263,397 B2 | 8/2007 | Hauck et al. |
| 7,276,064 B2 | 10/2007 | Paul et al. |
| 7,338,486 B2 | 3/2008 | Sliwa et al. |

(Continued)

FOREIGN PATENT DOCUMENTS

| | | |
|---|---|---|
| EP | 1 070 480 A2 | 1/2001 |
| EP | 1 508 300 A1 | 2/2005 |

(Continued)

OTHER PUBLICATIONS

Non-Final Office Action mailed Dec. 11, 2015; Related U.S. Appl. No. 14/703,460.

(Continued)

*Primary Examiner* — Weiwen Yang
(74) *Attorney, Agent, or Firm* — Theresa A. Raymer

(57) ABSTRACT

A method and system for displaying a three dimensional visualization of cardiac motion. The method and system obtain point specific (PS) motion data for a plurality of map points. The PS motion data indicates an amount of motion that occurred at the corresponding map point on a wall of the heart during at least one cardiac cycle. The method and system determine three dimensional (3D) positions of the map points during the cardiac cycle based on the PS motion data and select a set of 3D positions based on a frame rate. The method and system further generate 3D visualizations for each selected set of 3D positions.

24 Claims, 12 Drawing Sheets

(56) References Cited

U.S. PATENT DOCUMENTS

| | | |
|---|---|---|
| 7,386,339 B2 | 6/2008 | Strommer et al. |
| 7,505,809 B2 | 3/2009 | Strommer et al. |
| 7,697,973 B2 | 4/2010 | Strommer et al. |
| 7,881,769 B2 | 2/2011 | Sobe |
| 8,016,764 B1 | 9/2011 | Shelchuk |
| 2003/0093067 A1 | 5/2003 | Panescu |
| 2003/0233039 A1 | 12/2003 | Shao et al. |
| 2005/0154282 A1 | 7/2005 | Li et al. |
| 2006/0245536 A1 | 11/2006 | Boing |
| 2007/0073179 A1 | 3/2007 | Afonso et al. |
| 2007/0100332 A1 | 5/2007 | Paul et al. |
| 2007/0106146 A1* | 5/2007 | Altmann ............... A61B 5/042 600/407 |
| 2007/0181139 A1 | 8/2007 | Hauck |
| 2007/0244479 A1 | 10/2007 | Beatty et al. |
| 2007/0270705 A1 | 11/2007 | Starks |
| 2007/0299352 A1 | 12/2007 | Harlev |
| 2008/0009758 A1 | 1/2008 | Voth |
| 2008/0091193 A1 | 4/2008 | Kauphusman et al. |
| 2008/0190438 A1 | 8/2008 | Harlev |
| 2009/0163904 A1 | 6/2009 | Miller et al. |
| 2009/0171345 A1 | 7/2009 | Miller et al. |
| 2010/0168550 A1 | 7/2010 | Byrd et al. |
| 2010/0268059 A1 | 10/2010 | Ryu |
| 2011/0243401 A1* | 10/2011 | Zabair ..................... G06K 9/00 382/128 |
| 2012/0184863 A1 | 7/2012 | Harlev et al. |
| 2013/0222415 A1 | 8/2013 | Vilsmeier |
| 2013/0272592 A1 | 10/2013 | Eichler et al. |
| 2015/0045867 A1 | 2/2015 | Krishnan |
| 2015/0133802 A1 | 5/2015 | Nabutovsky et al. |
| 2015/0141765 A1 | 5/2015 | Razavi et al. |
| 2015/0141858 A1 | 5/2015 | Razavi et al. |

FOREIGN PATENT DOCUMENTS

| | | |
|---|---|---|
| EP | 2 757 528 A1 | 7/2014 |
| WO | 97/24981 A2 | 7/1997 |
| WO | 2012/090148 A1 | 7/2012 |

OTHER PUBLICATIONS

Non-Final Office Action mailed Sep. 30, 2015; Related U.S. Appl. No. 14/270,181.

Notice of Allowance mailed Dec. 8, 2015; Related U.S. Appl. No. 12/347,216.

Notice of Allowance mailed Jun. 22, 2015; Related U.S. Appl. No. 14/328,523.

Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.

International Search Report and Written Opinion in PCT Application No. PCT/US2015/028206 (Jul. 22, 2015).

Quatember, Bernhard et al., "Geometric Modeling and Motion Analysis of the Epicardial Surface of the Heart", Mathematics and Computers in Simulation, vol. 81, No. 3, pp. 608-622, Nov. 2010.

Segars, W. Paul et al., "A Realistic Spline-Based Dynamic Heart Phantom", IEEE Transactions on Nuclear Science, vol. 46, No. 3, pp. 503-506, Jun. 1999.

U.S. Appl. No. 09/107,731, filed Jun. 30, 1998 for "Chamber Mapping System".

Advisory Action mailed Aug. 10, 2015; Related U.S. Appl. No. 12/347,216.

Amendment filed Jun. 25, 2015; Related U.S. Appl. No. 12/347,216.

Final Office Action mailed May 4, 2015; Related U.S. Appl. No. 12/347,216.

Amendment filed Dec. 18, 2014; Related U.S. Appl. No. 12/347,216.

Non-Final Office Action mailed Oct. 2, 2014; Related U.S. Appl. No. 12/347,216.

Advisory Action mailed May 1, 2014; Related U.S. Appl. No. 12/347,216.

Amendment filed Apr. 24, 2014; Related U.S. Appl. No. 12/347,216.

Applicant Interview Summary, Apr. 21, 2014; Related U.S. Appl. No. 12/347,216.

Final Office Action mailed Feb. 25, 2014; Related U.S. Appl. No. 12/347,216.

Amendment filed Feb. 4, 2014; Related U.S. Appl. No. 12/347,216.

Non-Final Office Action mailed Nov. 21, 2013; Related U.S. Appl. No. 12/347,216.

Amendment filed Oct. 29, 2012; Related U.S. Appl. No. 12/347,216.

Advisory Action mailed Oct. 11, 2012; Related U.S. Appl. No. 12/347,216.

Amendment filed Oct. 1, 2012; Related U.S. Appl. No. 12/347,216.

Advisory Action mailed Sep. 12, 2012; Related U.S. Appl. No. 12/347,216.

Amendment filed Aug. 28, 2012; Related U.S. Appl. No. 12/347,216.

Final Office Action mailed Jun. 29, 2012; Related U.S. Appl. No. 12/347,216.

Amendment filed May 14, 2012; Related U.S. Appl. No. 12/347,216.

Interview Summary, Feb. 28, 2012; Related U.S. Appl. No. 12/347,216.

Non-Final Office Action mailed Feb. 13, 2012; Related U.S. Appl. No. 12/347,216.

Notice of Allowance mailed Oct. 27, 2015; Related U.S. Appl. No. 14/328,523.

Non-Final Office Action mailed Feb. 8, 2016; Related U.S. Appl. No. 14/270,181.

Notice of Allowance mailed Feb. 25, 2016; Related U.S. Appl. No. 14/328,513.

Notice of Allowance mailed Feb. 25, 2016; Related U.S. Appl. No. 14/703,760.

Non-Final Office Action mailed Mar. 28, 2016; Related U.S. Appl. No. 14/703,749.

Notice of Allowance mailed Apr. 19, 2016; Related U.S. Appl. No. 14/270,181.

* cited by examiner

_US 9,380,940 B2_

METHOD AND SYSTEM FOR DISPLAYING A THREE DIMENSIONAL VISUALIZATION OF CARDIAC MOTION

RELATED APPLICATION DATA

The present application is related to the following applications: U.S. provisional application Ser. No. 61/906,311, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. provisional application Ser. No. 61/910,630, filed Nov. 19, 2013, titled "METHOD TO MEASURE CARDIAC MOTION USING A CARDIOVASCULAR NAVIGATION SYSTEM", U.S. provisional application Ser. No. 61/906,305, filed Nov. 19, 2013, titled "METHOD TO IDENTIFY CARDIAC CYCLES WITH CONSISTENT ELECTRICAL RHYTHM AND MECHANICAL BEHAVIOR FOR COMPILATION INTO A REPRESENTATIVE CHARACTERIZATION OF CARDIAC MOTION", U.S. patent application Ser. No. 14/270,181, filed May 5, 2014, titled "METHOD AND SYSTEM TO CHARACTERIZE MOTION DATA BASED ON NEIGHBORING MAP POINTS", now U.S. Pub. No. 20150313511, U.S. patent application Ser. No. 14/270,186, May 5, 2014, titled "METHOD AND SYSTEM FOR CALCULATING STRAIN FROM CHARACTERIZATION DATA OF A CARDIAC CHAMBER", now U.S. Pub. No. US 20150313480, U.S. patent application Ser. No. 12/347,216, filed Dec. 31, 2008, titled "SYSTEM AND METHOD FOR RENDERING A MOTION MODEL OF A BEATING HEART", now U.S. Pat. No. 9,307,931, all of which are expressly incorporated herein by reference in their entirety.

BACKGROUND OF THE INVENTION

Embodiments of the present invention generally relate to methods and systems for cardiovascular navigation, and more particularly for displaying a three dimensional visualization of motion in a cardiac chamber or organ.

Cardiovascular navigation systems (CNS) provide real-time position and orientation information in relation to a part of the cardiovascular system, such as, the heart based on sensors placed at various locations within the cardiovascular system. The CNS may be integrated with a fluoroscopic (or other diagnostic) imaging system and track the sensors continuously within an imaging volume defined by the fluoroscopic system, on both live and pre-recorded background diagnostic images, Recently, it has been proposed to utilize the CNS to evaluate the motion of the heart and identify a desired (e.g., optimal) location for placement of a left ventricular (LV) lead and/or ablation target. For example, the CNS may systematically record information, such as displacement of the sensors, associated with various endocardial and epicardial locations of the LV. Epicardial locations may include mapping within the coronary sinus branches as well as mapping directly on the epicardial surface of the LV via a sub-xiphoid puncture technique, for example. Depending on the size of the heart and other factors during the procedure, there may be between 40 and 120 endocardial LV locations and up to 10 epicardial locations at which the MDG system obtains recordings for each patient.

Systems have been proposed to characterize the motion of the heart, specifically on the quantitative techniques of characterizing motion. However, to allow for qualitative and global evaluation of the three-dimensional motion of different segments of the LV there is a need for a visual identification of the latest activation site for lead placement and/or ablation targets.

SUMMARY

In accordance with an embodiment herein, a method is provided for displaying a three dimensional visualization of cardiac motion. The method includes obtaining point specific (PS) motion data for a plurality of map points. The PS motion data indicates an amount of motion that occurred at the corresponding map point on a wall of the heart during at least one cardiac cycle. The method further determines three dimensional (3D) positions of the map points during the cardiac cycle based on the PS motion data and selects a set of 3D positions based on a frame rate. Further, the method includes generating 3D visualizations of the PS motion data for each selected set of 3D positions.

In an embodiment, a system for displaying a three dimensional visualization of cardiac motion collected by a cardiovascular navigation system (CNS) is provided. The system includes a display and a plurality of physiological sensors configured to be positioned adjacent to a plurality of map points on a heart, wherein the physiological sensors acquire point specific (PS) motion data at the corresponding map points. The PS motion data indicates an amount of motion that occurred at the map points on a wall of the heart during at least one cardiac cycle. The system also includes a three dimensional (3D) analysis circuit module configured to determine 3D positions of the map points during the cardiac cycle based on the PS motion data. The 3D analysis circuit module is also configured to generate 3D visualizations of the PS motion data for a selected set of the 3D positions based on a frame rate. The 3D visualizations are shown in succession on the display.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Figure 1:
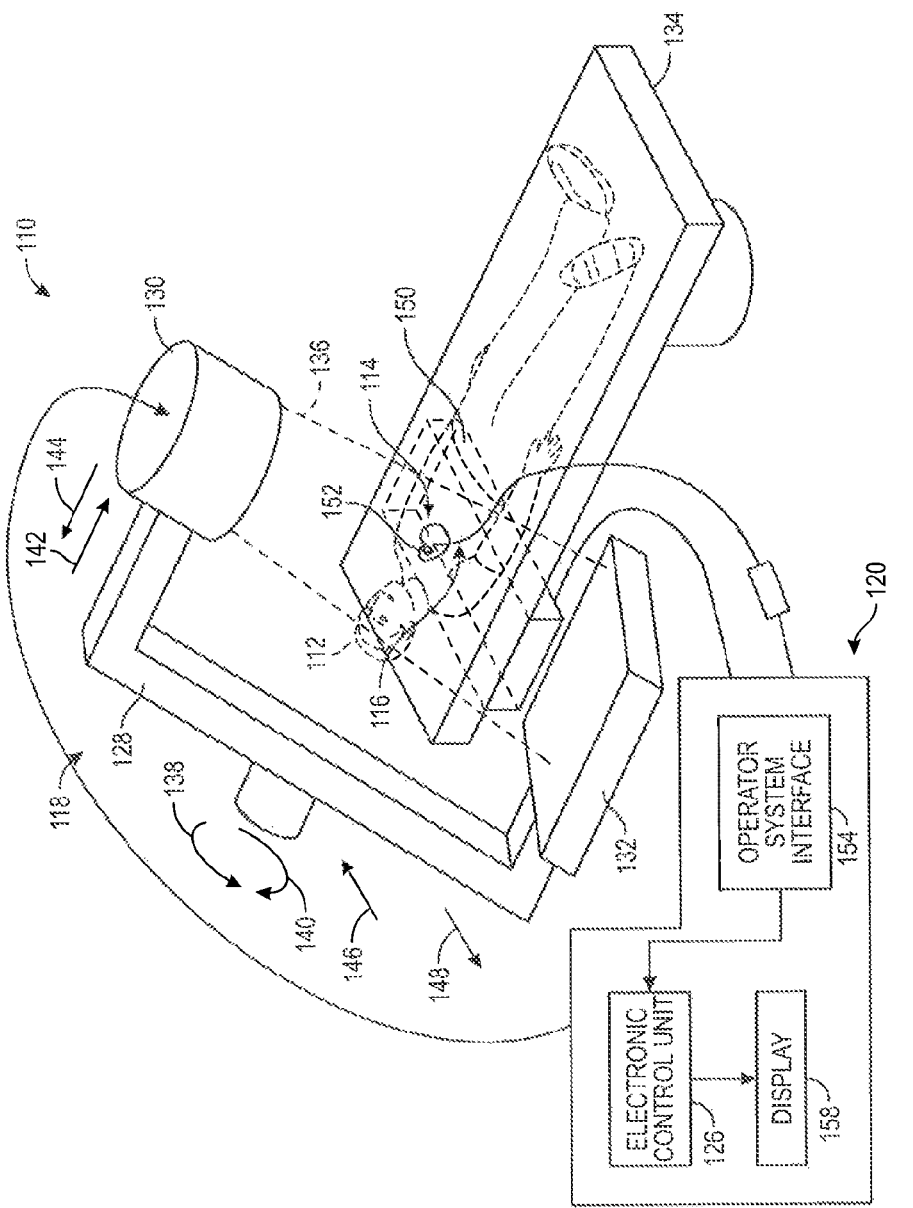
FIG. 1 illustrates a cardiovascular navigation system for use in imaging an anatomical region of the heart and to collect motion data, in accordance with an embodiment herein.

FIG. 1 illustrates a cardiovascular navigation system (CNS) 110, of an embodiment, for use in imaging an anatomical region of a patient 112, such as, a heart 114. A medical tool 116 is placed within the anatomical region, such as for example, an electrophysiological (EP) mapping catheter or a catheter generally described or shown in U.S. Pat. No. 7,881,769, which is expressly incorporated herein by reference. The medical tool 116 includes a plurality of electrophysiological sensors 152 that may be placed on the endocardial or epicardial surface of the left ventricle (LV) of the heart 114. The electrophysiological sensors 152 may be attached to the distal or proximal end of the medical tool 116, or any point in between. The electrophysiological sensors 152 measure a position and an electrical potential or an electric current of biological cells and tissues. The electrophysiological sensors 152 transmit the position and electrical potential information to an electronic control unit (ECU) 126. For example, the electrophysiological sensors 152 may be positioned by the medical tool 116 to measure point specific (PS) motion data for a plurality of map points of the wall of the heart 114. It should be understood, however, that the electrophysiological sensors 152 could be used in a variety of anatomical regions or alternative map points within the heart 114 or other organs in which motion characterization may be of interest.

Additionally or alternatively, the electrophysiological sensors 152 may be replaced by separate motion sensors and electrical sensors. The motion sensors in contact with the region of interest (e.g., the LV of the heart 114) measure the position sensors as well as the electrical sensors that are measuring the PS motion data of the region of interest. Optionally, the ECU 126 may receive the PS motion data and electrical sensor measurements simultaneously from the motion sensors and electrical sensors.

A navigation system 120 is provided to determine the position and orientation of the medical tool 116 within the body of the patient 112. In the illustrated embodiment, the navigation system 120 comprises a magnetic navigation system in which magnetic fields are generated in the anatomical region and position sensors associated with the medical tool 116 generate an output that is responsive to the position of the sensors within the magnetic field. The navigation system 120 may comprise, for example, the systems generally shown and described in, for example. U.S. Pat. Nos. 6,233,476, 7,197,354, 7,386,339, and 7,505,809 all of which are expressly incorporated by reference in their entirety. Although a magnetic navigation system is shown in the illustrated embodiment, it should be understood that the embodiments could find use with a variety of navigation systems including those based on the creation and detection of axes specific electric fields. The navigation system 120 may include a transmitter assembly 150.

The transmitter assembly 150 may include a plurality of coils arranged orthogonally to one another to produce a magnetic field in and/or around the anatomical region of interest. It should be noted that, although the transmitter assembly 150 is shown under the body of the patient 112 and under the table 134 in FIG. 1, the transmitter assembly 150 may be placed in another location, such as, attached to the radiation emitter 130, from which the magnetic field generators can project a magnetic field in the anatomical region of interest, In accordance with certain embodiments the transmitter assembly 150 is within the field of view 136. The ECU 126 may control the generation of magnetic fields by transmitter assembly 150.

The electrophysiological sensors 152 are configured to generate an output dependent on the relative position of electrophysiological sensors 152 within the field generated by the transmitter assembly 150. In FIG. 1, the electrophysiological sensor 152 and the medical tool 116 are shown disposed around the heart 114. The navigation system 120 determines the location of the electrophysiological sensors 152 within the generated field, and thus the position of the medical tool 116 as well. The navigation system 120 may further determine navigation coordinates, such as a Cartesian coordinate (e.g., (X, Y, Z)), of the navigation coordinate system.

The ECU 126 of the navigation system 120 may include or represent hardware circuits or circuitry that include and/or are connected with one or more logic based devices, such as processors, microprocessors, controllers, microcontrollers, or other logic based devices (and/or associated hardware, circuitry, and/or software stored on a tangible and non-transitory computer readable medium or memory). The ECU 126 may receive a plurality of input signals including signals generated by the medical tool 116, the electrophysiological sensors 152, an operator system interface 154 (e.g., graphical user interface, keyboard, touchscreen, mouse, or the like), and one or more patient reference sensors (not shown) and generate a plurality of output signals including those used to control the medical tool 116 and/or the display 158. The ECU 126 may also receive an input signal from an organ monitor (not shown), such as an ECG monitor, and sort or segregate images from an imaging system 118 based on a timing signal of a monitored organ. For example, ECU 126 may sort images based on the phase of the patient's cardiac cycle at which each image was collected, as more fully described in U.S. Pat. No. 7.697,973, which is hereby incorporated by reference in its entirety.

Optionally, the CNS 110 may include an imaging system 118. The CNS 110 may further include a registration system for registering a group of images of the anatomical region of the patient 112 in a navigation coordinate system of the navigation system 120 as generally described and shown in U.S. Patent Publication 2013/0272592 and International Pub. No.

WO 2012090148, the entire disclosure of which is expressly incorporated herein by reference.

Figure 5:
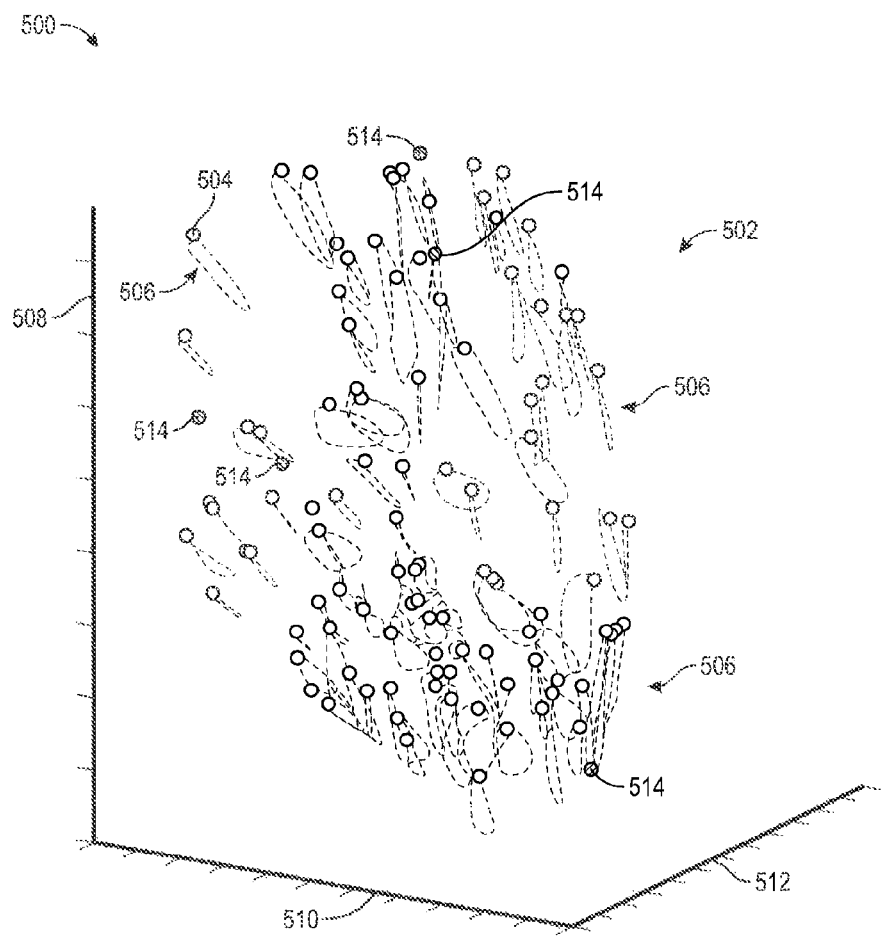
FIG. 5 illustrates a three dimensional visualization for a display corresponding to a group of map points generated for a frame of the cardiac cycle, in accordance with an embodiment disclosed herein.
Figure 6A:
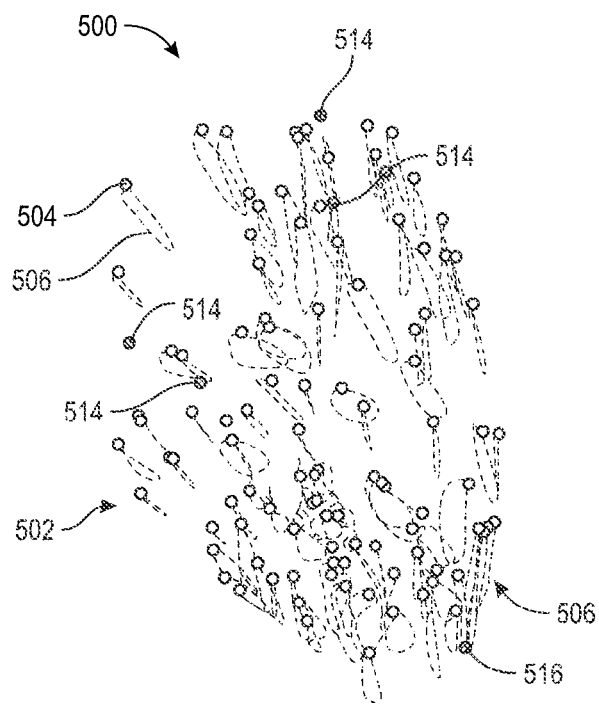
FIG. 6 illustrates four three dimensional visualizations corresponding to four frames of a group of map points for a display, in accordance with an embodiment disclosed herein.
Figure 6B:
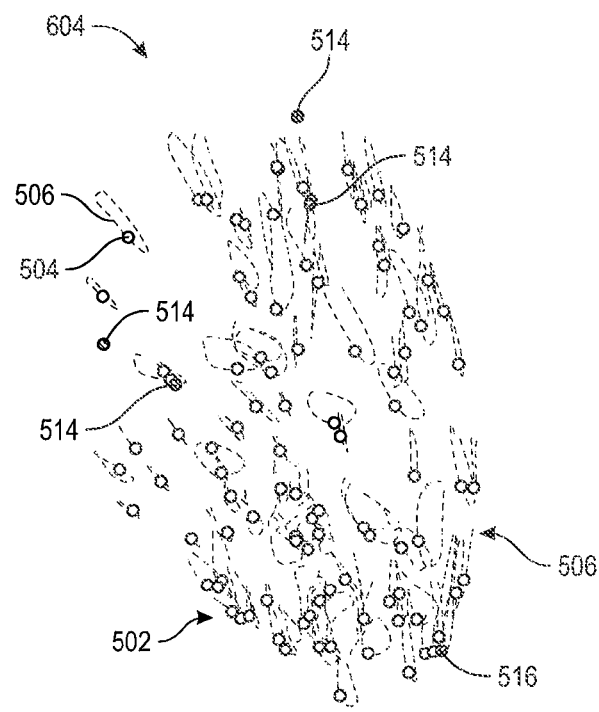
Figure 6C:
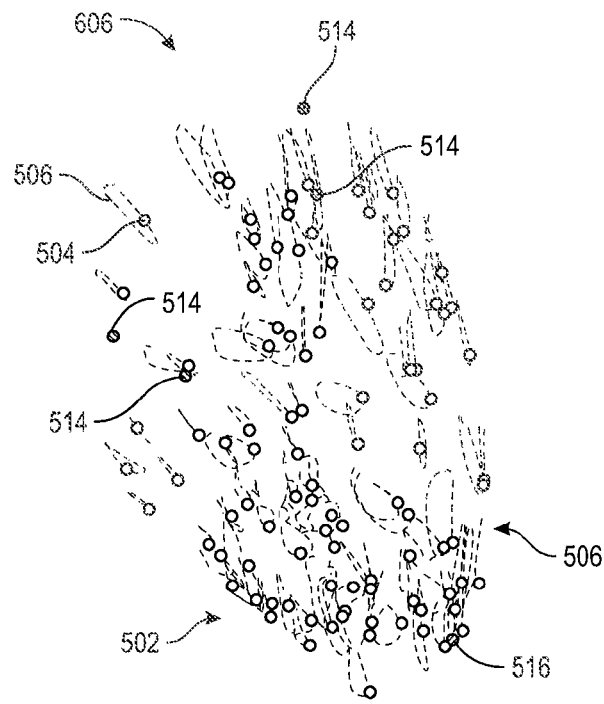
Figure 6D:
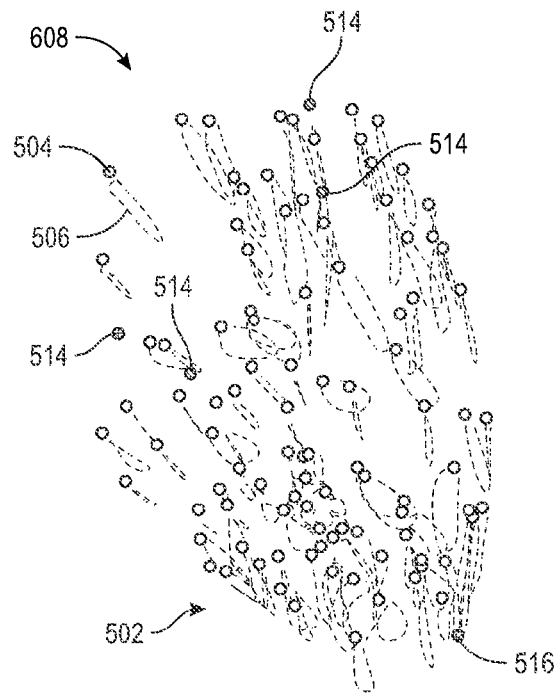

The imaging system 118 may be provided to acquire images of the heart 114 or another anatomical region of interest (e.g., anatomical landmark points 514, 516 in FIG. 5). The imaging system 110 may, for example, comprise of a fluoroscopic imaging system. Additionally or alternatively, rather than a fluoroscopic imaging system, computed tomography (CT) imaging systems, a three-dimensional radio angiography (3DRA) system, and the like may be used. Although the imaging system 118 is described herein for an exemplary embodiment of the invention, the imaging system 118 is not required for the inventive subject matter described within this application The imaging system 118 may include a C-arm support structure 128, a radiation emitter 130, and a radiation detector 132. The emitter 130 and detector 132 are disposed on opposite ends of the support structure 128 and disposed on opposite sides of the patient 112 as the patient 112 lays on an operation table 134. The emitter 130 and detector 132 define a field of view 136 and are positioned such that the field of view 136 includes the anatomical region of interest as the patient 112 lays on the operation table 134. The imaging system 118 is configured to capture images of anatomical features and other objects within the field of view 136. The support structure 128 may have freedom to rotate about the patient 112 as shown by lines 138 and 140. The support structure 128 may also have freedom to slide along lines 142 and 144 (e.g., along the cranio-caudal axis of the patient 112) and/or along lines 146 and 148 (e.g., perpendicular to the cranio-caudal axis of the patient 112). Rotational and translational movement of the support structure 128 yields corresponding rotational and translational movement of the field of view 136. Additionally or alternatively, the navigation system 120 may adjust the navigation coordinates of the position of the medical tool 116 to compensate for changes in the C-arm support structure 128 and respiratory movements of the patient as disclosed in the U.S. Provisional Application No. 61/910,630, entitled, "METHOD TO MEASURE CARDIAC MOTION USING A CARDIOVASCULAR NAVIGATION SYSTEM," which is expressly incorporated herein by reference in its entirety.

The imaging system 118 may acquire a group of images of an anatomical region of the patient 112 by first shifting along lines 142, 144, 146, and/or 148 to place the anatomical region of interest within the field of view 136. Second, the support structure 128 may rotate the radiation emitter 130 and the radiation detector 132 about the patient 112, keeping the anatomical region within the field of view 136. The imaging system 118 may capture images of the anatomical region as the support structure 128 rotates, providing a group of two dimensional images of the anatomical region from a variety of angles. The group of images may be communicated to the ECU 126 for image processing and display. The group of images may comprise a sequence of images taken over a predetermined time period.

Additionally, one or more patient reference sensors (not shown) may be on the body of the patient 112, for example, on the chest. The patient reference sensors measure a displacement and orientation of the patient reference sensors relative to a predetermined reference point, such as, the electrophysiological sensors 152 or the transmitter assembly 150.

Figure 2:
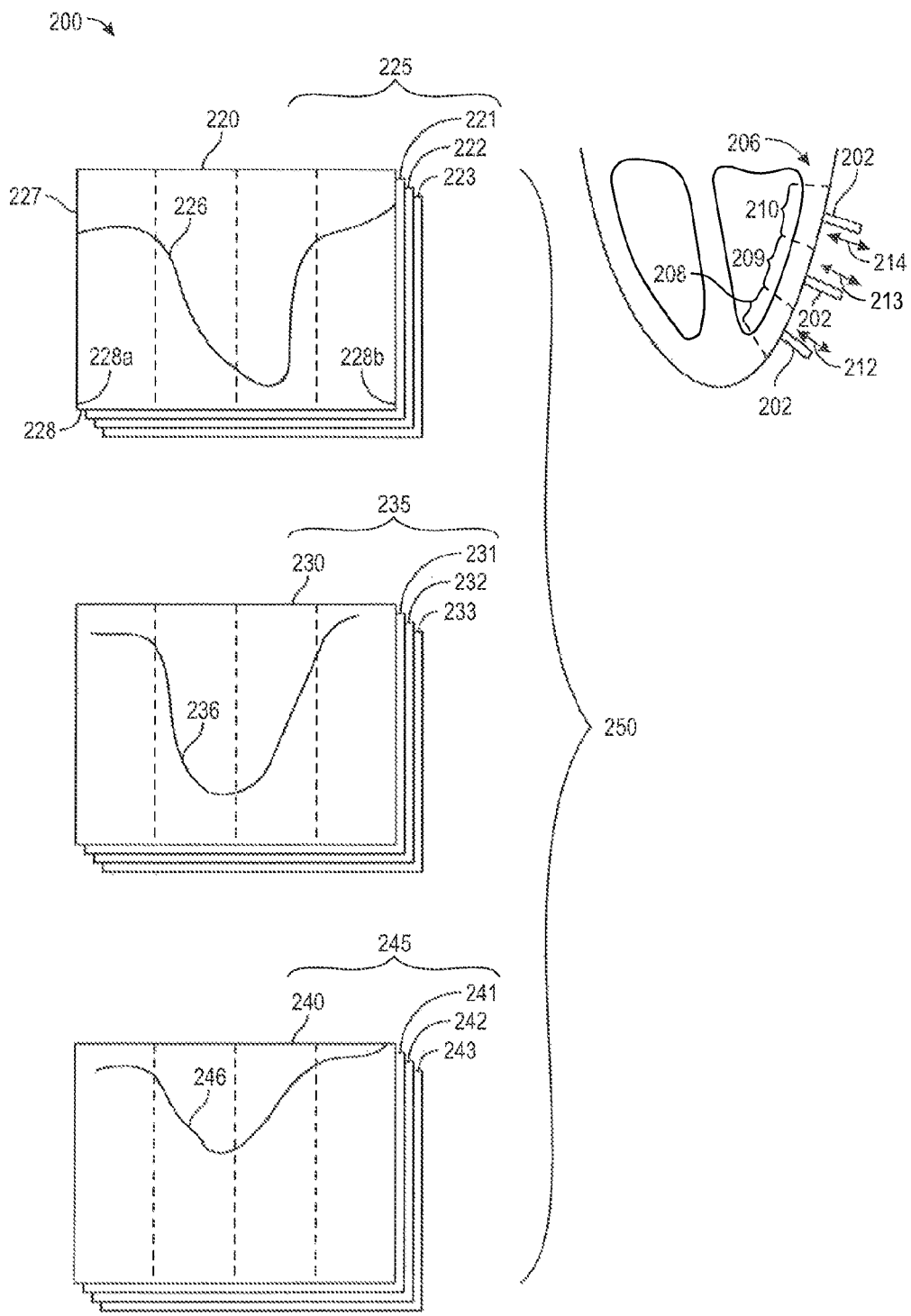
FIG. 2 illustrates a graphical representation of a plurality of map points of a heart.

As stated above, the electrophysiological sensors 152 may acquire PS motion data of the heart 114 at numerous map points, positioned along the walls of the various chambers during at least one cardiac cycle. Optionally, the map points may be obtained in the coronary sinus and its tributaries. FIG. 2 illustrates a graphical representation of a plurality of map points associated with a portion of a heart 200, such as a heart wall 206, for which it is desirable to measure PS motion data. The term "point specific" is used to indicate that the motion data is associated with a single select location on the heart wall. The data values represent positions of the single select location over one or more cardiac cycles. The heart wall 206 may be separated or divided into map points 208-210. The example of FIG. 2 shows three map points of interest 208-210 along the wall of the left ventricle. Optionally, more or fewer map points of interest may be designated. A tool 202 (e.g., the medical tool 116 with the plurality of electrophysiology sensors 152) is positioned directly against the heart wall 206 at one or more points within each map point of interest 208-210. The tool 202 measures movement of the one or more points over a select period of time. In the example of FIG. 2, the tool 202 is shown positioned against a point of interest in each map point 208-210 at different points in time.

For example, the tool 202 is positioned, during a first measuring operation, at a point within the map point 208 while collecting PS motion data associated with movement (e.g., along the arrow 212) by the map point 208. The movement may be in various linear, transverse, or rotational directions. Next, the tool 202 may be positioned, during a second measuring operation, at a point within the map point 209 while collecting PS motion data associated with movement (e.g., along the arrow 213) by the map point 209. Next, the tool 202 is positioned, during a third measuring operation, at a point within the map point 210 while collecting PS motion data associated with movement (e.g., along the arrow 214) by the map point 210.

The position of the tool 202 may be continuously monitored by a navigation system (e.g., the navigation system 220) to obtain sets of motion data associated with each map point 208-210 over a select period of time, such as, during at least one cardiac cycle. In FIG. 2, a motion waveform subset 220 is collected during one cardiac cycle while the tool 202 is held against the LV wall acquiring PS motion data for a point within the map point 208. The PS motion data may define a motion waveform 226 at the map point 208. The motion waveform 226 may represent a displacement of the map point 208, illustrated with respect to a vertical axis 227 axis representing an amount of displacement of the map point 208 from a start reference position, during the cardiac cycle, illustrated along a horizontal axis 228 representing time from a beginning 228a to an end 228b of the cardiac cycle. Optionally, the tool 202 may be held against the LV wall at a point within the map point 208 for multiple heart beats or cardiac cycles thereby generating multiple motion waveform subsets 220-223 (e.g., for four consecutive heart beats). Optionally, the PS motion data subsets 220-223 may be collected for fewer than or more than four heart beats. The PS motion data subsets 220-223 associated with the map point 208 may be grouped to form a collection 225 of motion waveform subsets 220-223 associated with a single map point 208.

Once a desired amount of motion data is collected for the map point 208, the tool 202 is moved to a next desired position, such as at a point within the map point 209. Next, the data collection process is repeated to obtain PS motion data forming a motion waveform 236 indicative of an amount of motion experienced or displacement of the map point 209 over a cardiac cycle (e.g., heart beat). Optionally, the tool 202 may be held for multiple heart beats to obtain PS motion data subsets 230-233 over a corresponding number of heart beats (e.g., cardiac cycles).

Once a desired amount of motion data is collected for the map point 209, the tool 202 is moved to a next desired position such as at a point within the map point 210. Next, the data collection process is repeated to obtain PS motion data forming a motion waveform 246 indicative of an amount of motion experienced or displacement of the map point 210 over a cardiac cycle (e.g., heart beat). Optionally, the tool 202 may be held for multiple heart beats to obtain PS motion data subsets 240-243 over a corresponding number of heart beats (e.g., cardiac cycles). The motion waveform subsets 230-333, and 240-243, which are associated with map points 209 and 210, may be grouped to form collections 235 and 245, respectively, associated with single map points 209 and 210. The plurality of motion waveform subsets 220-243 for all map points 208-210 of interest of the heart wall 206 may collectively define a motion data set 250.

Optionally, more map points of the heart wall 206 may be studied to collect additional motion waveform subsets of motion data. For example, the walls of the right ventricular, right atrium, and/or left atrium may also be divided into map points, for which motion data is collected.

A cardiovascular navigation system (e.g., CNS 110) collects the PS motion data from one or more tools 202 and may perform pre-processing on the PS motion data. For example, the CNS 110 may filter or remove PS motion data subsets (e.g., 220-223) or motion waveforms (e.g., 226) acquired during irregular (e.g., based on the waveform shape, amplitude, timing, duration) or invalid beats (e.g., ectopic beats). The ECU 126 may receive electrical sensor measurements of the patient 112 from a 12-lead surface electrocardiogram (ECG), body surface mapping (BSM), subcutaneous ECG, a uni- or bi-polar intracardiac electrograms (IEGMs) of a catheter, such as the medical tool 116, placed in the coronary sinus (CS), right ventricular (RV apex), or the like. The ECU 126 may identify the invalid or irregular beats from the electrical sensor measurements and remove the invalid or irregular beats with the corresponding PS motion data subset acquired during the beat from the collection as disclosed in U.S. Provisional Application No. 61/906,305, entitled, "METHOD TO IDENTIFY CARDIAC CYCLES WITH CONSISTENT ELECTRICAL RHYTHM AND MECHANICAL BEHAVIOR FOR COMPILATION INTO A REPRESENTATIVE CHARACTERIZATION OF CARDIAC MOTION," which is expressly incorporated herein by reference in its entirety.

Optionally, the CNS 110 may adjust the motion waveform subsets 225, 235, 245 to extend over a common time interval. For example, the motion waveform subsets 225, 235, 245 may be temporally equalized by "stretching" the motion waveforms that have shorter cycle lengths until the shorter motion waveform subsets have a length equal to the predetermined interval. The common time interval may be predetermined, or automatically selected, such as by choosing a length corresponding to the longest, shortest, or average length of the motion waveform subset 220-223. The time interval may be set to begin at a point in time defined by a global signal such as the peak of the R-wave as detected by using the Electrocardiogram (ECG) or Intracardiac Electrogram (IEGM) signals as disclosed in the U.S. Provisional Application No. 61/910,630, entitled, "METHOD TO MEASURE CARDIAC MOTION USING A CARDIOVASCULAR NAVIGATION SYSTEM," which is expressly incorporated herein by reference in its entirety. Optionally, the time interval may be defined to begin based on another global marker of electrical activity (e.g., the T-wave, P-wave).

Additionally or alternatively, the CNS 110 may average the PS motion data subsets 220-223 to determine an average motion waveform for the map point 208 as disclosed in U.S. Provisional Application No. 61/906,305, entitled, "METHOD TO IDENTIFY CARDIAC CYCLES WITH CONSISTENT ELECTRICAL RHYTHM AND MECHANICAL BEHAVIOR FOR COMPILATION INTO A REPRESENTATIVE CHARACTERIZATION OF CARDIAC MOTION," which is expressly incorporated herein by reference in its entirety. For example, the motion waveform subsets 220-223 may be combined through averaging or otherwise. Optionally, the motion data 250, which is utilized in connection with embodiments described hereafter, may include information indicative of a radial component of wall movement, and/or may include information indicative of a longitudinal component of wall movement. Optionally, the motion data may include information associated with 3-dimensional (3-D) movement calculated as a 3-D distance from an initial position at a select starting point in the cardiac cycle, such as an R-wave or local electrical activation time.

Figure 3:
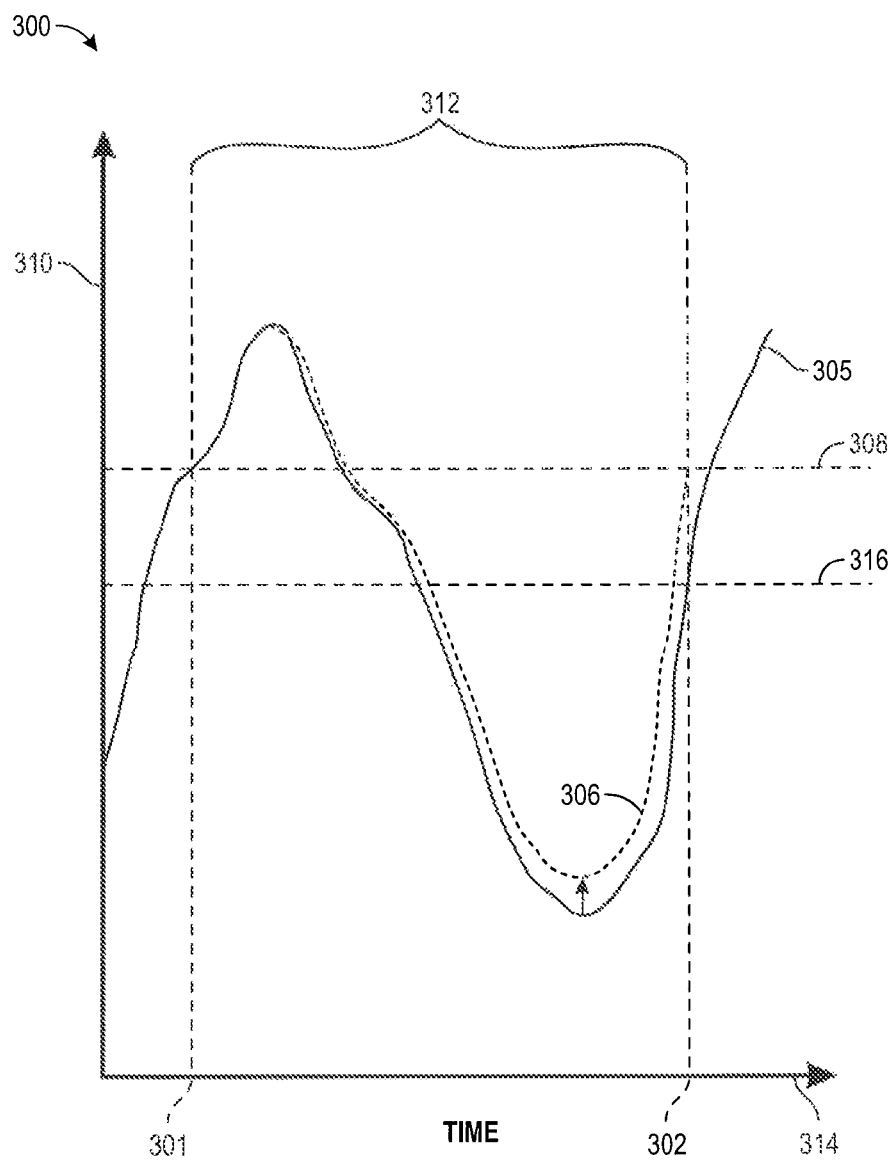
FIG. 3 illustrates a motion waveform associated with a map point being rotated, in accordance with an embodiment herein.

Additionally or alternatively, the CNS 110 may apply a rotation technique to the motion waveform subsets 225, 235, 245 to correct for non-periodicity. A periodic motion waveform (e.g., the motion waveform 226, 236, 246) of a map point during the cardiac cycle has at the beginning 228a and end 228b of the cardiac cycle 228 approximately the same measured displacement or position. Non-periodicity may occur from errors in the acquired PS motion data for the map point that defines the motion waveform. For example, if the electrophysiological sensor 252 is not directly against the heart wall during the entire cardiac cycle the motion waveform may drift. FIG. 3 illustrates a motion waveform 305 (e.g., motion waveform 226) defined by a plurality of PS motion data acquired at a map point. The motion waveform 305 may represent a displacement of the map point with respect to a vertical axis 310, representing an amount of displacement of the map point, during a cardiac cycle 312 along a horizontal axis 314. At a start 301 of the cardiac cycle 312, the motion waveform 305 has a measured displacement at 308. At an end 302 of the cardiac cycle 312, the motion waveform 305 has a measured displacement at 316. The difference in the displacements of the motion waveform 305 at the start 301 and the end 302 of the cardiac cycle 312 shows that the motion waveform 305 is non-periodic. The rotation technique may be applied to generate a rotated motion waveform 306 that results in a periodic motion waveform as disclosed in U.S. Provisional Application No. 61/910,630, entitled, "METHOD TO MEASURE CARDIAC MOTION USING A CARDIOVASCULAR NAVIGATION SYSTEM," which is expressly incorporated herein by reference in its entirety.

Figure 4:
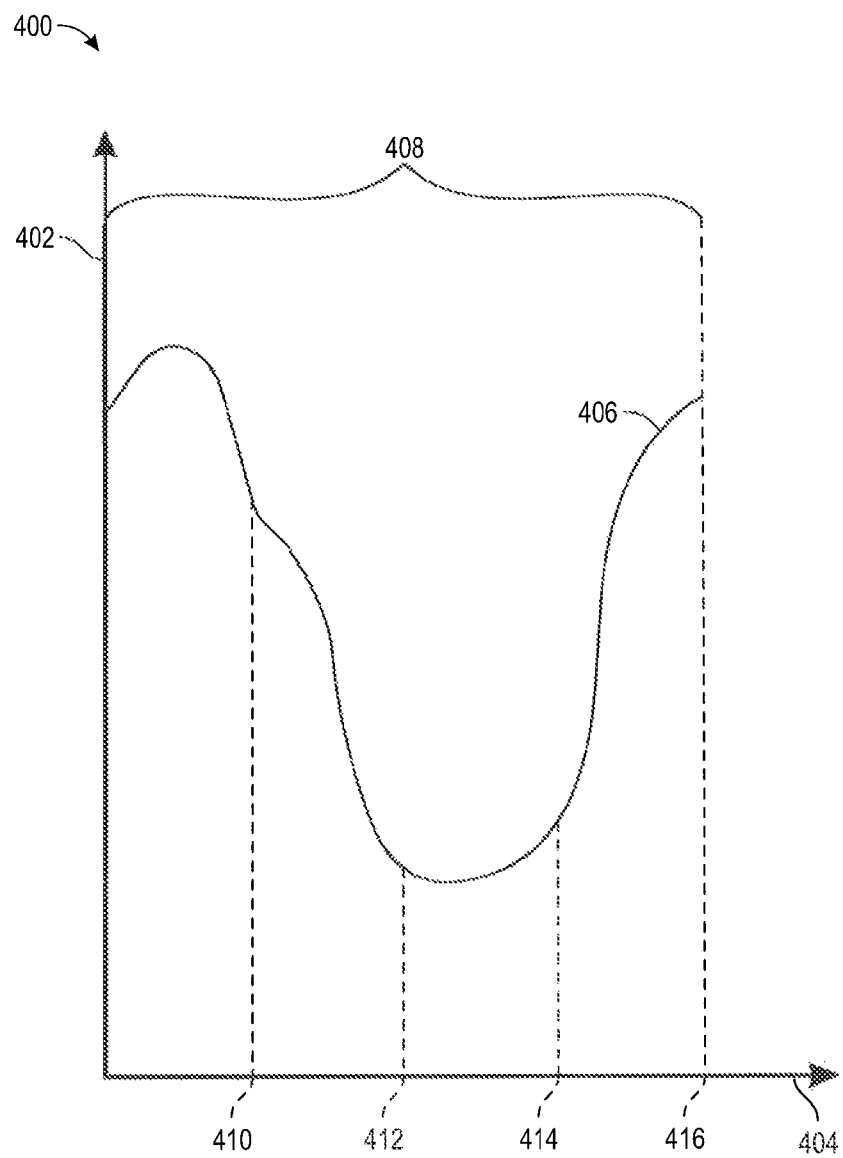
FIG. 4 illustrates a post processed motion waveform associated with a map point being rotated, in accordance with an embodiment herein.

FIG. 4 illustrates a single motion waveform 406 defined by PS motion data from a data motion set (e.g., the data motion set 250) acquired from a group of map points 502 after one or more pre-processing steps (e.g., rotation technique, stretching, correspond to a regular cardiac beat) have been completed to the data motion set by the CNS 110. The pre-processing steps adjust or remove PS motion data such that motion waveforms defined by the remaining and/or adjusted PS motion data of the data motion set exhibit the same cardiac cycle length 408 and/or the same number of PS motion data samples for the cardiac cycle. The motion waveform 406 may represent a displacement of a map point 504 (FIG. 5) over the cardiac cycle. The motion waveform 406 is illustrated with respect to a vertical axis 402 axis, which may represent an amount of displacement of the map point 504 during a cardiac cycle, and a horizontal axis 404 representing time.

The navigation system 120 may determine the Cartesian coordinates (e.g., (X, Y, Z)) correlating to the position of each map point (e.g., 504) from the group of map points 502 during the cardiac cycle, as described above, by measuring the position of the electrophysiological sensors 152 positioned adjacent to a corresponding map point. From the Cartesian coordinates the navigation system 120 may generate a three dimensional (3D) plot 500 of the group of map points 502 at select frames to be viewed on the display 158.

FIG. 5 illustrates the 3D visualization 500 for the display 158 corresponding to a group of map points 502 generated by the navigation system 120 for a frame 410 of the cardiac cycle, in accordance with an embodiment disclosed herein. The 3D visualization 500 is shown oriented with a Y-axis 508, an X-axis 510, and a Z-axis 512. The position of each map point for a particular frame is illustrated as an icon (e.g., black dot, circle) or graphical marker. The 3D visualization 500 illustrates the position of each map points for a frame. For example, for the map point 504, the 3D visualization 500 illustrates the position of the map point 504 at the frame 410, which is shown in relation to the motion waveform 406 in FIG. 4. The frame 410 represents a set sample from the pre-processed PS motion data. The frame 410 may be selected after a set number of samples of the pre-processed PS motion data at a frame rate. The frame rate may be predetermined by the navigation system 120 or set by the clinician through the operator system interface 154. The frame rate may be a specified integer value less than or equal to the number of pre-processed PS motion data samples. The navigation system 120 may divide or sample the pre-processed PS motion data at the frame rate.

For example, the navigation system 120 may acquire the position measurements from the electrophysiological sensors 152 corresponding to the map point 504 every 1 millisecond with a predetermined frame rate of 200. During the cardiac cycle 408 of 1 second, the navigation system 120 may have acquired 1000 samples representing the PS motion data acquired for the map point 504. After the pre-processing, the pre-processed PS motion data may include 800 samples. The navigation system 120 may select four frames, frames 410, 412, 414, and 416, from the pre-processed PS motion data by sampling the pre-processed PS motion data every 200 samples, which corresponds to the frame rate. Once the frames are selected, the navigation system 120 may generate separate 3D visualizations for each frame (e.g., 500, 604, 606, 608). It should be noted that the sample rate, the length of the cardiac cycle, as well as the frame rate may be larger or less than the above example.

In alternative embodiments, the pre-processed PS motion data may not be divisible by the frame rate as in the example above. The navigational system 120 may round the indices to the nearest integer that is less than or equal to a ratio of the pre-processed PS motion data over the frame rate.

The 3D visualization 500 may further include a plurality of landmark points 514, 516 corresponding to a physical feature or anatomical structure of the heart. The landmark points 514, 516 may correspond to a static or stationary point that does not change position during the cardiac cycle. Additionally or alternatively, the landmark points 514, 516 may be used as a stationary visual reference to the group of map points 502, which may change positions at various times during the cardiac cycle. The position or Cartesian coordinate of the landmark points 514, 516 may be determined using the operator system interface 154 or automatically from the ECU 126. For example, the imaging system 118 may provide images of the LV, which are displayed on the display 158. The user (e.g., clinician) may select a plurality of locations or a specific structure (e.g., from a drop down menu) corresponding to an anatomical structure, such as, the mitral annulus and/or the apex of the left ventricle (LV) within the image using the operator system interface 154. The ECU 126 may overlay graphical markers based on the user selections within the 3D visualization 500, such as placing or highlighting the landmark points 514, 516 corresponding to the mitral annulus and the apex, respectively. It should be noted, in embodiments the landmark points 514, 516 may change position or have motion during the cardiac cycle. The movement of the landmark points 514, 516 may represented as part of the 3D visualization, similar to the map points 504 having, for example, a different color or graphical marker than the map points 504 as described below.

Additionally or alternatively the 3D visualization 500 may include trajectory loops 506 for each map point (e.g., 504). The trajectory loops 506 illustrate the trajectory or travel path of the map points from the beginning to the end of the cardiac cycle. FIG. 6 illustrate four 3D visualizations 500, 604, 606, 608 corresponding to four frames 410, 412, 414, and 416, respectively, of the group of map points 502 for the display 158, in accordance with an embodiment. For each 3D visualization 500, 604, 606, 608, the group of map points 502 traverse along the trajectory loops 506 corresponding to the position of the map points 502 of the frames 410, 412, 414, and 416, respectively.

The navigation system 120 may continually update the 3D visualization 500, 604, 606, 608 corresponding to the frames 410, 412, 414, and 416 on the display 158. The display 158 may be updated or transition to an alternative 3D visualization 500, 604, 606, 608 at a pre-defined speed to form a dynamic movie illustrating the motion of the group of map points 502 during the cardiac cycle 408. Optionally, the navigation system 120 may synchronize the frames 410, 412, 414, and 416 with a surface ECG signal to correlate the mechanical behavior (e.g., the 3D visualizations 500, 604, 606, 608) with the overall electrical signal acquired by the surface ECG. Additionally or alternatively, the navigation system 120 may change or adjust the icon or graphical marker of the map point (e.g., 504) to depict a timing or extent aspects (e.g., mechanical activation time) of the 3D motion of the map points.

Figure 7:
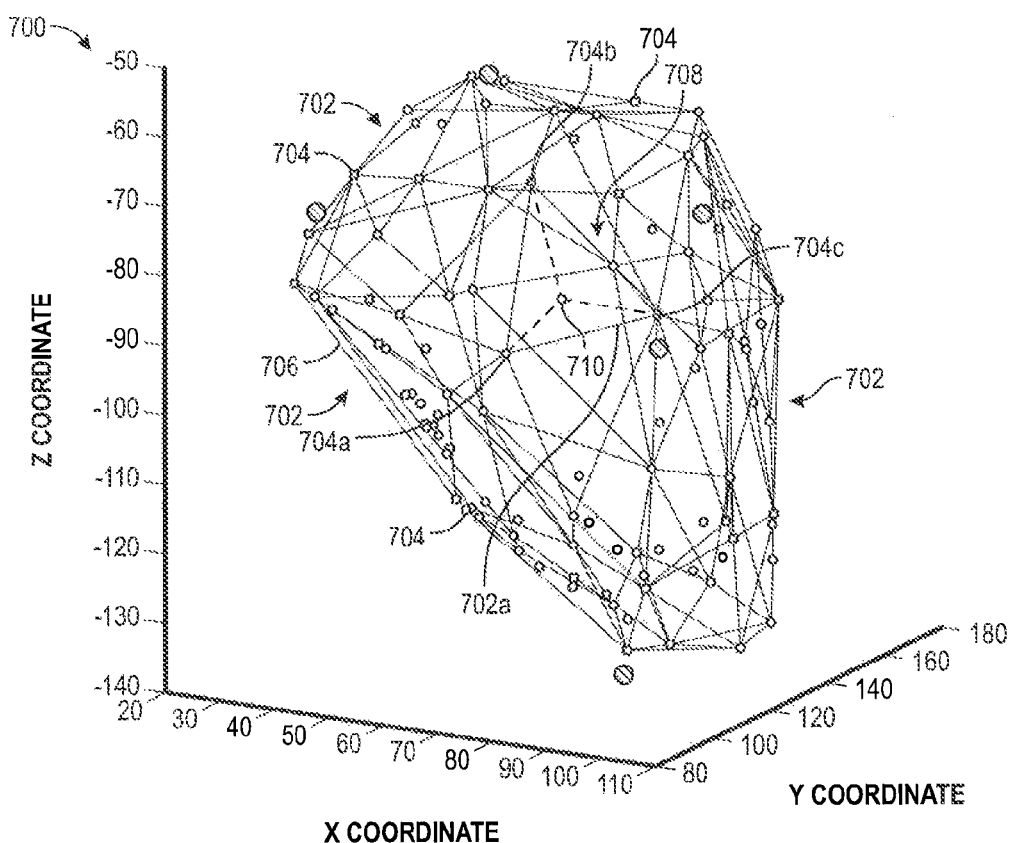
FIG. 7 illustrates a set of non-overlapping space-filling three dimensional tetrahedrons from a group of map points, in accordance with an embodiment disclosed herein.
Figure 8:
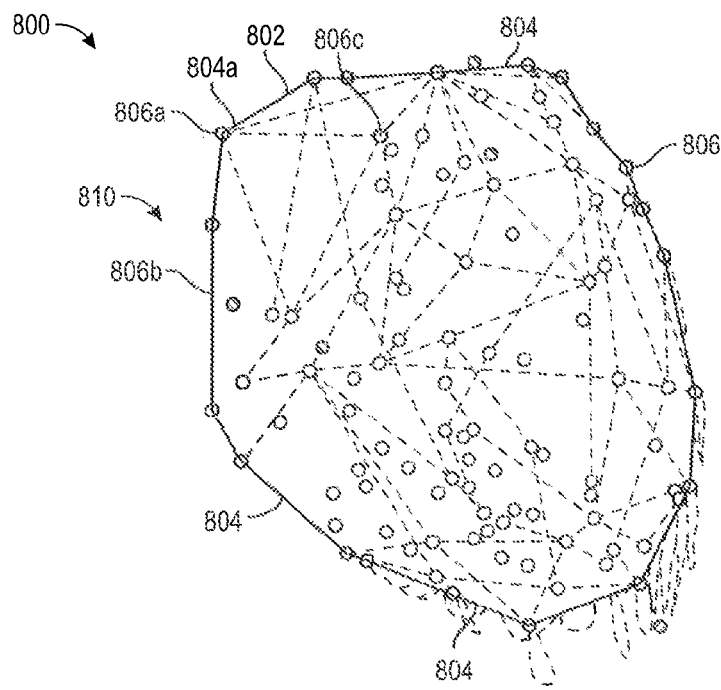
FIG. 8 illustrates a shell enclosing a three dimensional visualization of a group of map points for a display, in accordance with an embodiment disclosed herein.
Figure 9A:
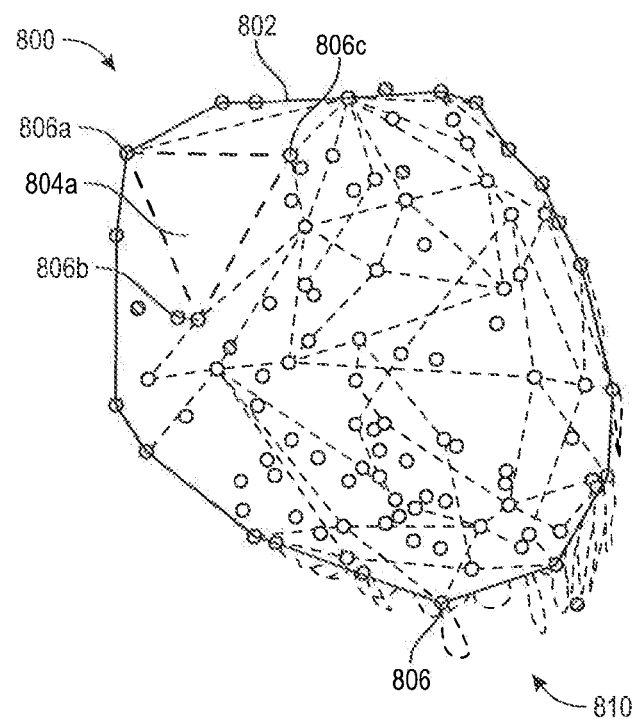
FIG. 9 illustrates shells enclosing four three dimensional visualizations corresponding to four frames of a group of map points for a display, in accordance with an embodiment disclosed herein.
Figure 9B:
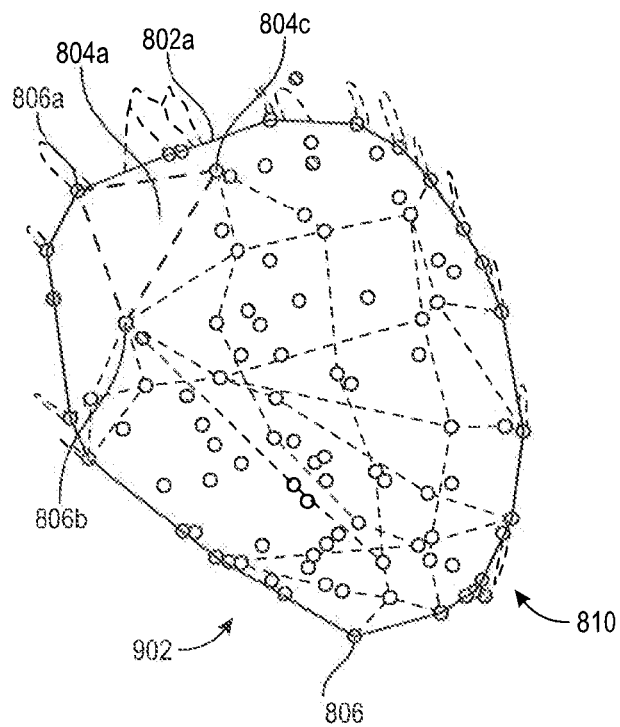
Figure 9C:
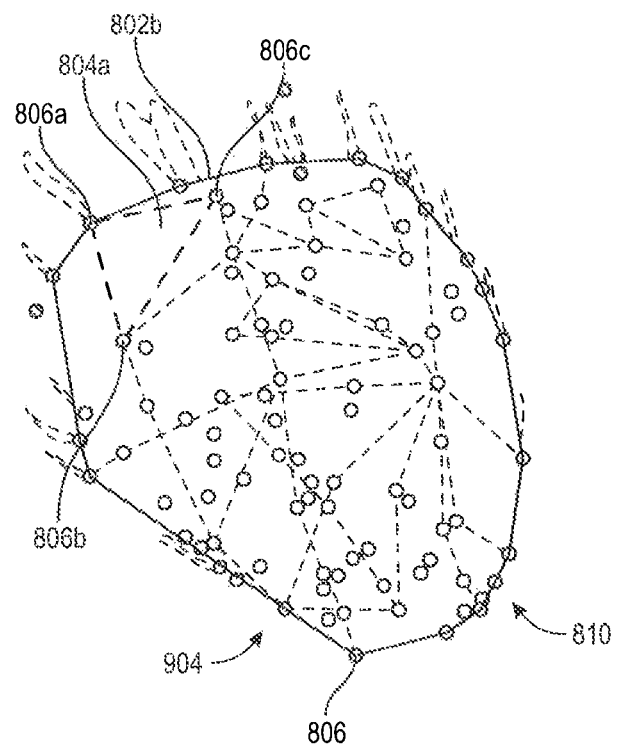
Figure 9D:
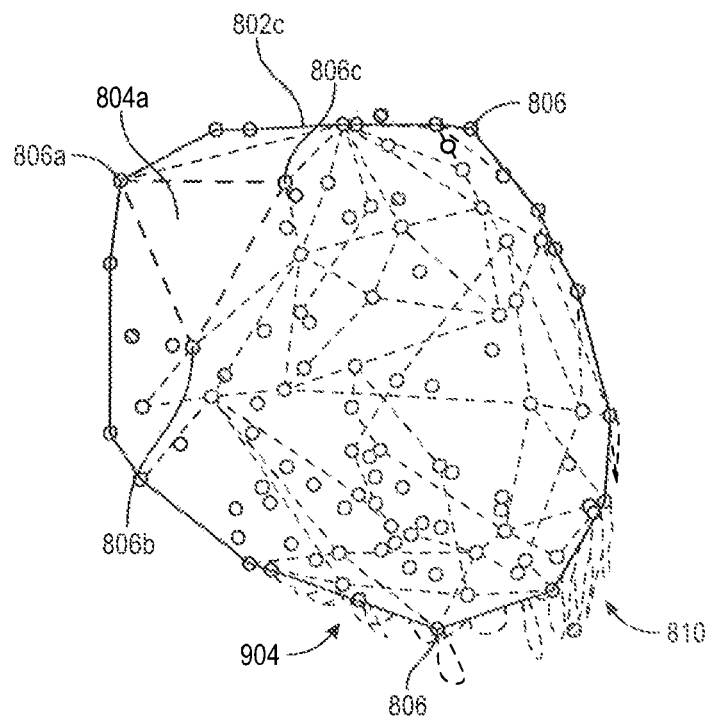

Additionally or alternatively, the navigation system 120 may apply a triangulation technique algorithm (e.g., DeLaunay algorithm) to generate a shell 802 (FIG. 8) enclosing a 3D visualization 800 of a group of map points 806. The navigation system 120 may apply the triangulation technique algorithm to a single reference frame (e.g., 410) or repeat the triangulation at every frame considered (e.g., 410, 412, 414, 416). The navigation system 120 may create a set of non-overlapping space-filling 3D tetrahedrons 702 as illustrated in a 3D visualization 700 in FIG. 7. The 3D tetrahedrons 702 are formed using the pre-processed PS motion data positions of map points 704 (e.g., the group of map points 502) set at a synced time-point (e.g., peak of the R-wave) or a frame 810 (e.g., 410, 412, 414, 416). From the set of 3D tetrahedrons 702, the navigation system 120 may identify an outermost boundary 706, which encloses a volume 708. The shell 802 may be formed by the navigation system 120 from the outermost boundary 706 as a series of two dimensional (2D) triangles, for example, using a convex hull definition. By way of example, the boundary that is defined by all of the 3D tetrahedrons may be a surface that is comprised of 2D triangles made from three map points. The navigation system 120 may then graph the shell 802 by filling triangular surface areas 804 that are defined by three map points. For example, the navigation system 120 may fill the triangular surface area 804*a* defined by the three map points 806*a-c*. It should be noted, that although the shell 802 is shown with a level of transparency to view the group of map points 806, in alternative embodiments the level of the transparency may be increased or decreased by the clinician through the operator system interface 154

In an embodiment, the navigation system 120 may dynamically adjust the shell 802 to other frames 902-904 (FIG. 9) based on the change in the position of the group map points 806 at each frame 902-904 forming the triangular surface areas 804. For example, the position and size of the triangular surface area 804a defined by the three map points 806a-c is adjusted for each frame 810, 902-906 due to the change in position of the map points 806a-c at each frame 810, 902-906. Additionally or alternatively, the adjustment of the shell 802 for each frame 810, 902-906 may be transitioned on the display 158 at a pre-defined speed to form a dynamic movie illustrating the 3D motion the cardiac chamber measured by the electrophysiological sensor 152. Optionally, the dynamic motion of the shell 802 may be synced with an electrical signal (e.g., ECG) such that the user can see the electrical behavior at different frames. Additionally or alternatively, the triangular surface areas 804 defined by the three map points (e.g., the map points 806a-c) may be a pre-determined color set by the navigation system 120. Optionally, the navigation system 120 may adjust the color of select triangular surface areas to reflect quantitative characteristics of that region, such as, the time to onset of mechanical activation or the average extent of radial motion, Additionally or alternatively, the navigation system 120 may continually measure the volume within the shell 802 by calculating the sum of each individual 3D tetrahedron 702 included within the shell 802. For example, the navigation system 120 may determine the volume of the 3D tetrahedron 702a with vertices at the position of the map points 704a-c and a vertex 710 from Equation 1. Where the variable a is the Cartesian coordinate (e.g., X, Y, Z) of the map point 704a, the variable b is the Cartesian coordinate of the map point 704b, the variable c is the Cartesian coordinate of the map point 704c, and the variable d is the Cartesian coordinate of the vertex 710.)

$$v=(1/6)*|\det(a-d,b-d,c-d)| \quad \text{(Equation 1)}$$

Figure 10:
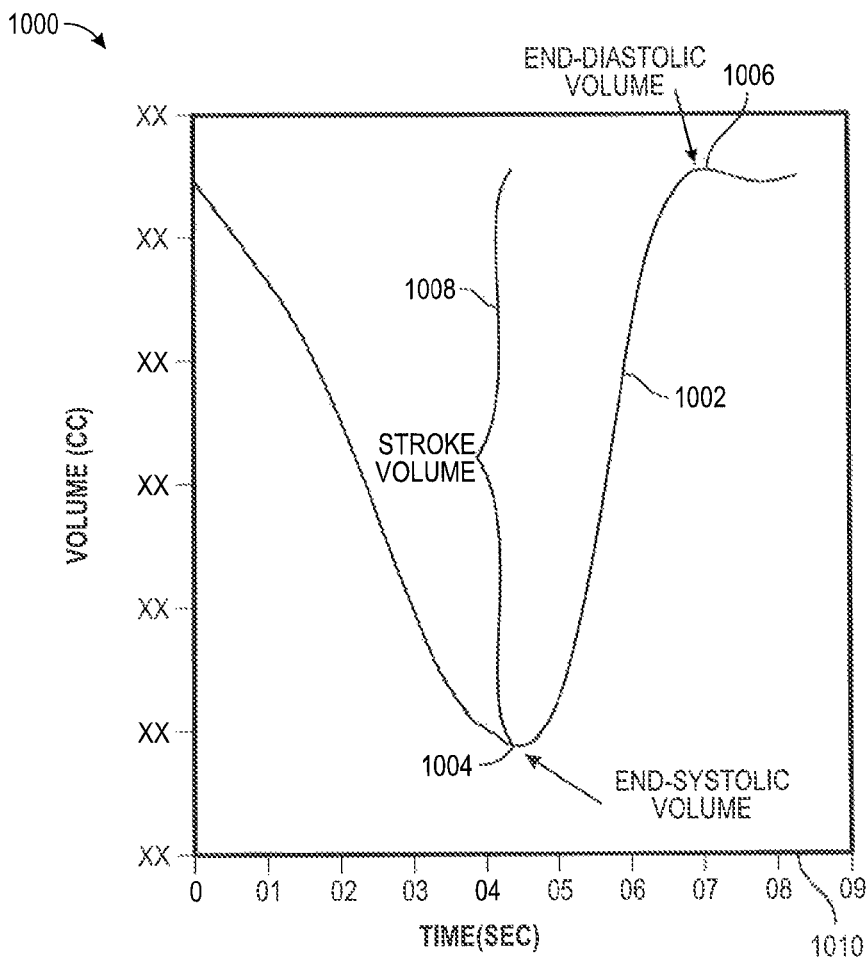
FIG. 10 illustrates a plot of a volume of a shell during a cardiac cycle, in accordance with an embodiment disclosed herein.

Based on the dynamic volume measurements 1002 of the shell 802, the navigation system 120 may determine an end-systolic volume (ESV) 1004, end-diastolic volume (EDV) 1006, ejection fraction (EF), and stroke volume (SV) 1008 at a temporal resolution of, for example 30 Hz. FIG. 10 illustrates a plot 1000 of the dynamic volume measurements 1002 of the shell 802 determined by the navigation system 120 over time 1010. From the dynamic volume measurements 1002, the navigation system 120 may determine the ESV 1004 as the minimum volume encompassed by the shell during the cardiac cycle. Additionally or alternatively, the navigation system 120 may determine the ESV 1004 based on a pre-determined time during the end-systolic of the chamber of the heart monitored. The pre-determined time may be set time after the peak of the QRS complex (e.g., R-wave), such as approximately 30% of the cycle length, based on an independent electrical (e.g., ECG) or mechanical activity of the heart. It should be noted, in embodiments the pre-determined time be set at more than or less than 30% of the cycle length.

Optionally, from the dynamic volume measurements 1002, the navigation system 120 may determine the EDV 1006 as the maximum volume encompassed by the shell during the cardiac cycle. Additionally or alternatively, the navigation system 120 may determine the EDV 1006 based on a pre-determined time during the end-systolic of the chamber of the heart monitored.

The pre-determined time may be set time after the peak of the QRS complex (e.g., R-wave), such as approximately 70% of the cycle length, based on an independent electrical (e.g., ECG) or mechanical activity of the heart. Optionally, the navigation system 120 may determine the SV 1008 by subtracting the ESV 1004 from the EDV 1006. It should be noted, in embodiments the pre-determined time may be more than or less than 70% of the cycle length. Optionally, the navigation system 120 may determine the EF by dividing the SV 1008 by the EDV 1006.

In an embodiment, the navigation system 120 may calculate a two dimensional (2D) dynamic cross-section of the PS motion data from a data motion set (e.g., the data motion set 250) acquired from a group of map points 502 after one or more pre-processing steps (e.g., rotation technique, stretching, correspond to a regular cardiac beat) have been completed to the data motion set by the CNS 110. The navigation system 120 may implement a 2D triangulation technique to generate a convex hull. The convex hull representing the cross-sectional perimeter of the cardiac chamber. The convex hull may be used by the navigation system 120 to determine a cross-sectional area of the convex hull.

In an embodiment, the map points may be obtained in the coronary sinus and its tributaries. The map points, positioned within each branch may be used by the navigation system 120 to create a separate shell for each branch. The navigation system 120 may link the shells together such that a dynamic tree structure is created.

Figure 11:
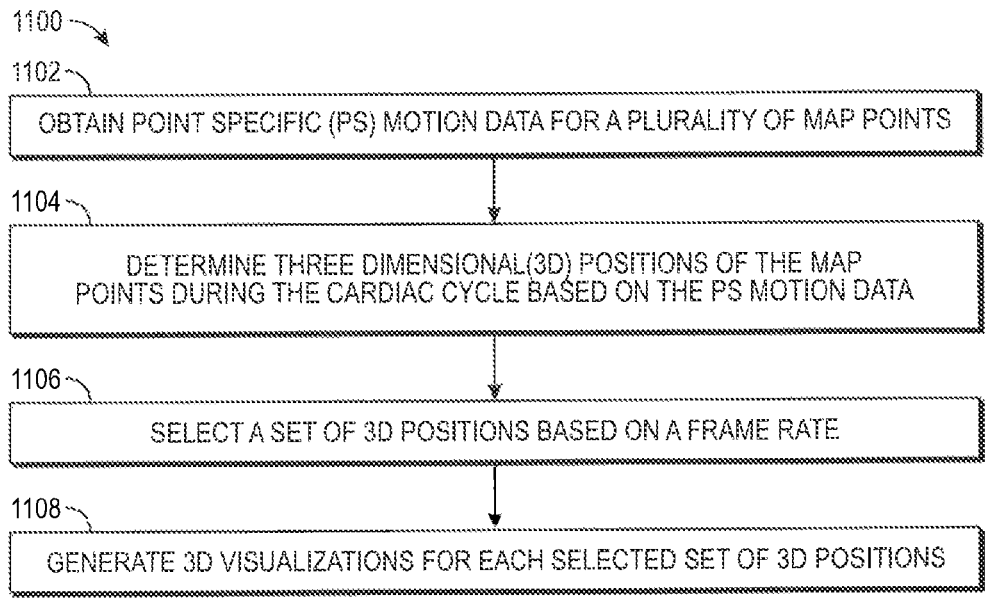
FIG. 11 illustrates a flow chart of a method for dynamic visualization of three dimensional motion cardiac motion, in accordance with an embodiment herein.

FIG. 11 illustrates a flowchart of a method 1100 for characterizing motion data collected by a cardiovascular navigation system (CNS). The method 1100, for example, may employ structures or aspects of various embodiments (e.g., systems and/or methods) discussed herein (e.g., the CNS 110 in FIG. 1). In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Furthermore, it is noted that the following is just one possible method of characterizing motion data collected by the CNS 110. It should be noted, other methods may be used, in accordance with an embodiment herein.

Beginning at 1102, the method 1100 obtains point specific (PS) motion data for a plurality of map points (e.g., 504). The PS motion data may be acquired or collected using the cardiovascular navigation system (CNS) 110 with the electrophysiological sensor 152 in real-time or prior to implementation of FIG. 11.

At 1104, the method 1100 determines 3D positions of the map points during the cardiac cycle based on the PS motion data. For example, the navigation system 120 may determine the Cartesian coordinates (e.g., (X, Y, Z)) correlating to the position of each map point (e.g., 504) from the group of map points 502 during the cardiac cycle, as described above, by measuring the position of the electrophysiological sensors 152 positioned adjacent to a corresponding map point.

At 1106, the method 1100 selects a set of 3D positions based on a frame rate. At 1108, the method 1100 generates 3D visualizations for each selected set of 3D positions. For example, the navigation system 120 selects the frame 410 or sample of the pre-processed PS motion data at a frame rate. The frame 410 may include the group of map points 502 each having a 3D position. The navigation system 120 may generate a 3D visualization 500 for the display 158 corresponding to a group of map points 502 for the frame 410 of the cardiac cycle.

Figure 12:
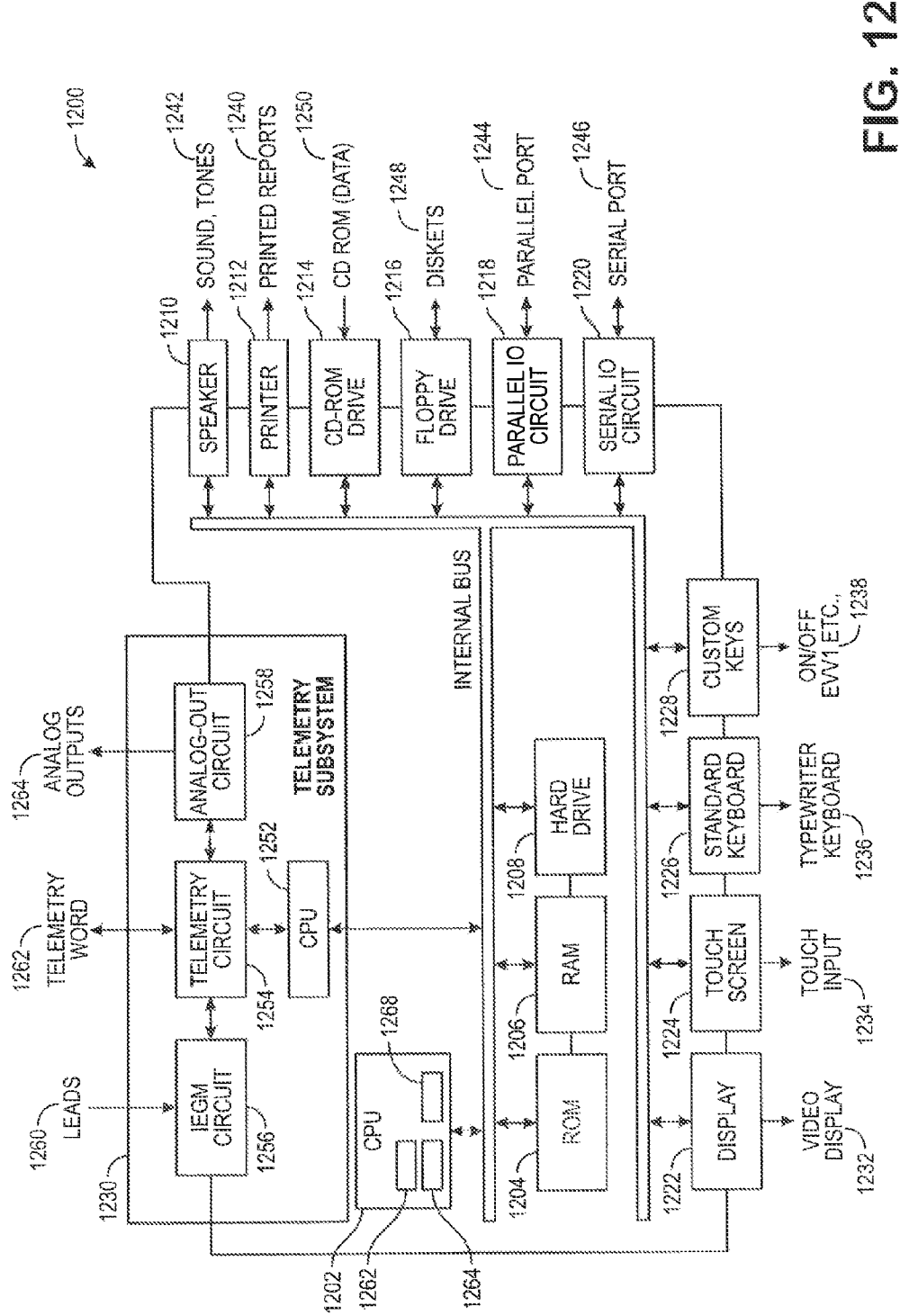
FIG. 12 illustrates a system for analyzing motion data in accordance with an embodiment.

FIG. 12 illustrates a functional block diagram of an embodiment of an electronic control unit (ECU) 1200 that is operated in accordance with the processes described herein to analyze motion data and to interface with the CNS 110. The ECU 1200 may be a workstation, a portable computer, a PDA, a cell phone and the like. The ECU 1200 includes an internal bus that connects/interfaces with a Central Processing Unit (CPU) 1202, ROM 1204, RAM 1206, a hard drive 1208, the speaker 1210, a printer 1212, a CD-ROM drive 1214, a floppy drive 1216, a parallel I/O circuit 1218, a serial I/O circuit 1220, the display 1222, a touch screen 1224, a standard keyboard connection 1226, custom keys 1228, and a telemetry subsystem 1230. The internal bus is an address/data bus that transfers information between the various components described herein. The hard drive 1208 may store operational programs as well as data, such as waveform templates and detection thresholds.

The CPU 1202 typically includes a microprocessor, a micro-controller, or equivalent control circuitry, and may interface with the CNS 110. The CPU 1202 may include RAM or ROM memory, logic and timing circuitry, state machine circuitry, and I/O circuitry to interface with the CNS 110. The display 1222 (e.g., may be connected to the video display 1232). The touch screen 1224 may display graphic information relating to the CNS 110. The display 1222 displays various information related to the processes described herein. The touch screen 1224 accepts a user's touch input 1234 when selections are made. The keyboard 1226 (e.g., a typewriter keyboard 1236) allows the user to enter data to the displayed fields, as well as interface with the telemetry subsystem 1230. Furthermore, custom keys 1228 turn on/off 1238 (e.g., EVVI) the ECU 1200. The printer 1212 prints copies of reports 1240 for a physician to review or to be placed in a patient file, and speaker 1210 provides an audible warning (e.g., sounds and tones 1242) to the user. The parallel I/O circuit 1218 interfaces with a parallel port 1244. The serial I/O circuit 1220 interfaces with a serial port 1246. The floppy drive 1216 accepts diskettes 1248. Optionally, the floppy drive 1216 may include a USB port or other interface capable of communicating with a USB device such as a memory stick. The CD-ROM drive 1214 accepts CD ROMs 1250.

The CPU 1202 is configured to analyze PS motion data collected by the CNS 110 for a plurality of map points to determine a 3D representation of the map points for the display 1222. The CPU 1202 includes a 3D analysis circuit module 1264 that is configured to determine 3D positions of the map points during the cardiac cycle based on the PS motion data and generate a 3D representation of the map points. The CPU 1202 also includes a shell generation circuit module 1262 that may generate a shell to enclose the map points of the 3D representation from the 3D analysis circuit module 1264, as explained herein. The CPU 1202 also includes a volume analysis circuit module 1268 that may determine the volume of the shell, as explained herein.

The telemetry subsystem 1230 includes a central processing unit (CPU) 1252 in electrical communication with a telemetry circuit 1254, which communicates with both an IEGM circuit 1256 and an analog out circuit 1258. The circuit 1256 may be connected to leads 1260. The circuit 1256 may also be connected to implantable leads to receive and process IEGM cardiac signals. Optionally, the IEGM cardiac signals sensed by the leads may be collected by the CNS 110 and then transmitted, to the ECU 1200, wirelessly to the telemetry subsystem 1230 input.

The telemetry circuit 1254 is connected to a telemetry wand 1262. The analog out circuit 1258 includes communication circuits to communicate with analog outputs 1264. The ECU 1200 may wirelessly communicate with the CNS 110 and utilize protocols, such as Bluetooth, GSM, infrared wireless LANs, HIPERLAN, 3G, satellite, as well as circuit and packet data protocols, and the like. Alternatively, a hard-wired connection may be used to connect the ECU 1200 to the CNS 110.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hard-wired to perform the methods or portions of the methods described herein, and/or when the processors (e.g., of the devices described herein) operate according to one or more software programs that are written by one or more persons of ordinary skill in the art to perform the operations described in connection with the methods.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

The invention claimed is:

1. A method for displaying a three dimensional visualization of cardiac motion, the method comprising:
   obtaining point specific (PS) motion data for a plurality of map points, wherein the PS motion data indicates an amount of motion that occurred at the corresponding map point on a wall of the heart during at least one cardiac cycle;
   determining three dimensional (3D) positions of the map points during the cardiac cycle based on the PS motion data;
   selecting sets of 3D positions for corresponding frames of the cardiac cycle; and
   generating 3D visualizations for the selected sets of 3D positions, wherein the 3D visualizations illustrate trajectory loops for the map points over at least a portion of the cardiac cycle.

2. The method of claim 1, further comprising synchronizing the 3D visualizations with an electrical signal measuring electrical activity of the heart.

3. The method of claim 1, further comprising generating a set of non-overlapping space-filling 3D tetrahedrons defined by the 3D positions of the map points within each 3D visualization, wherein the 3D tetrahedron includes three map points defining an outermost boundary of the corresponding 3D visualization; and
   defining a shell for each 3D visualization from the outermost boundaries of the 3D tetrahedrons.

4. The method of claim 3, further comprising determining a volume defined by the shell.

5. The method of claim 4, wherein the determined volume represents at least one of an end systolic volume, or an end diastolic volume.

6. The method of claim 4, further comprising determining at least one of a stroke volume or ejection fraction based on the volume of at least two shells.

7. The method of claim 1, wherein each of the trajectory loops illustrates a travel path of the corresponding map point from a beginning to an end of the cardiac cycle.

8. The method of claim 3, wherein the shell is represented having a color and/or transparency, the color is based on a quantitative motion measurement.

9. The method of claim 1, wherein the map points are represented as a graphical icon having a color, the color is based on a quantitative motion measurement.

10. The method of claim 1, wherein the generating the 3D visualizations includes generating the trajectory loops for a corresponding group of the map points based on a position of the map points in multiple frames of the cardiac cycle.

11. A system for displaying a three dimensional visualization of cardiac motion collected by a cardiovascular navigation system (CNS), the system comprising:
   a display;
   a plurality of physiological sensors configured to be positioned adjacent to a plurality of map points on a heart, wherein the physiological sensors acquire point specific (PS) motion data at the corresponding map points, the PS motion data indicates an amount of motion that occurred at the map points on a wail of the heart during at least one cardiac cycle; and
   a three dimensional (3D) analysis circuit module configured to determine 3D positions of the map points during the cardiac cycle based on the PS motion data, the 3D analysis circuit module configured to generate 3D visualizations for a selected set of the 3D positions for corresponding frames of the cardiac cycle, the 3D visualizations illustrating trajectory loops for the map points over at least a portion of the cardiac cycle, the 3D visualizations are shown in succession on the display.

12. The system of claim 11, wherein the 3D visualizations are synchronized with an electrical signal measuring electrical activity of the heart.

13. The system of claim 11 further comprising a shell generation circuit module configured to generate a set of non-overlapping space-filling 3D tetrahedrons defined by the 3D positions of the map points within each 3D visualization, wherein the 3D tetrahedron includes three map points defining an outermost boundary of the corresponding 3D visualization, the shell generation circuit module is further configured to define a shell for each 3D visualization from the outermost boundaries of the 3D tetrahedrons.

14. The system of claim 11, further comprising a volume analysis circuit module configured to determine a volume defined by the shell.

15. The system of claim 14, wherein the determined volume represents at least one of an end systolic volume, or an end diastolic volume.

16. The system of claim 14, wherein the volume analysis circuit module is configured to determine at least one of a stroke volume or ejection fraction based on the volume of at least two shells.

17. The system of claim 11, wherein each of the trajectory loops illustrates a travel path of the corresponding map point from a beginning to an end of the cardiac cycle.

18. The system of claim 13, wherein the she is represented having a color and/or transparency, the color is based on a quantitative motion measurement.

19. The system of claim 11, wherein the map points are represented as a graphical icon having a color, the color is based on a quantitative motion measurement.

20. The system of claim 11, wherein the 3D analysis circuit generates the trajectory loops for a corresponding group of the map points based on a position of the map points in multiple frames of the cardiac cycle.

21. The method of claim 3, further comprising dynamically adjusting the shell based on a change in a position of a corresponding group of map points at frames.

22. The method of claim 3, further comprising transitioning the display to adjust the shell for each of the frames at a pre-defined speed to form a dynamic movie illustrating 3D motion of the wall.

23. The system of claim 13, wherein the shell generation circuit module us configured to dynamically adjust the shell based on a change in a position of a corresponding group of map points at frames.

24. The system of claim 13, wherein the shell generation circuit module us configured to transition the display to adjust the shell for each of the frames at a pre-defined speed to form a dynamic movie illustrating 3D motion of the wall.

\* \* \* \* \*